(12) United States Patent
Metcalf et al.

(10) Patent No.: US 8,562,651 B2
(45) Date of Patent: Oct. 22, 2013

(54) SACROILIAC TERMINAL ANCHOR DEVICE AND METHOD

(75) Inventors: Newton Metcalf, Memphis, TN (US); Nicholas Benson, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 42 days.

(21) Appl. No.: 13/075,679

(22) Filed: Mar. 30, 2011

(65) Prior Publication Data
US 2012/0253398 A1    Oct. 4, 2012

(51) Int. Cl.
A61B 17/70    (2006.01)

(52) U.S. Cl.
USPC ............... 606/264; 606/266; 606/315

(58) Field of Classification Search
USPC .................................. 606/301–321
See application file for complete search history.

(56) References Cited

U.S. PATENT DOCUMENTS

| | | | | |
|---|---|---|---|---|
| 4,870,957 A * | 10/1989 | Goble et al. | ............... | 623/13.12 |
| 5,658,285 A * | 8/1997 | Marnay et al. | ................. | 606/264 |
| 5,941,880 A | 8/1999 | Errico et al. | | |
| 6,156,037 A * | 12/2000 | LeHuec et al. | ................. | 606/247 |
| 6,368,326 B1 * | 4/2002 | Dakin et al. | ................... | 606/103 |
| 6,517,542 B1 * | 2/2003 | Papay et al. | .................... | 606/232 |
| 7,144,413 B2 * | 12/2006 | Wilford et al. | ................. | 606/232 |
| 8,343,189 B2 * | 1/2013 | Assell et al. | .................... | 606/247 |
| 2001/0007941 A1 * | 7/2001 | Steiner et al. | .................... | 606/69 |
| 2002/0128712 A1 * | 9/2002 | Michelson | ................. | 623/17.11 |
| 2004/0147929 A1 * | 7/2004 | Biedermann et al. | ........... | 606/61 |
| 2007/0233122 A1 * | 10/2007 | Denis et al. | ..................... | 606/73 |
| 2009/0082810 A1 | 3/2009 | Bhatnagar et al. | | |
| 2009/0306779 A1 * | 12/2009 | Ahn | .......................... | 623/17.11 |
| 2010/0106200 A1 | 4/2010 | Stark | | |
| 2012/0209331 A1 * | 8/2012 | Michelson | .................... | 606/264 |

OTHER PUBLICATIONS

Cunningham, Bryan W.; Lewis, Stephen, J.; Long, John; Dmitriev, Anton E.; Linville, Douglas A,; Bridwell, Keith H; ,Biomechanical evaluation of lumbosacral reconstruction techniques for spondylolisthesis, SPINE0362-2436; 2002, vol. 27, No. 21, pp. 2321-2327 [7 page(s) (article)] (23 ref.).

* cited by examiner

Primary Examiner — Jerry Cumberledge

(57) ABSTRACT

A spinal stabilization apparatus and method according to which an anchor element is engaged with a bone structure of a spinal system. The anchor element defines a reservoir adapted to contain a bone-growth promoting material and the reservoir is in fluid communication with the bone structure via at least one aperture defined in the anchor element. A rod-connecting element extend from the anchor element and is adapted to extend outward from the bone structure to engage at least a portion of a rod when the rod extends within a vicinity of the spinal system and the bone structure.

12 Claims, 8 Drawing Sheets

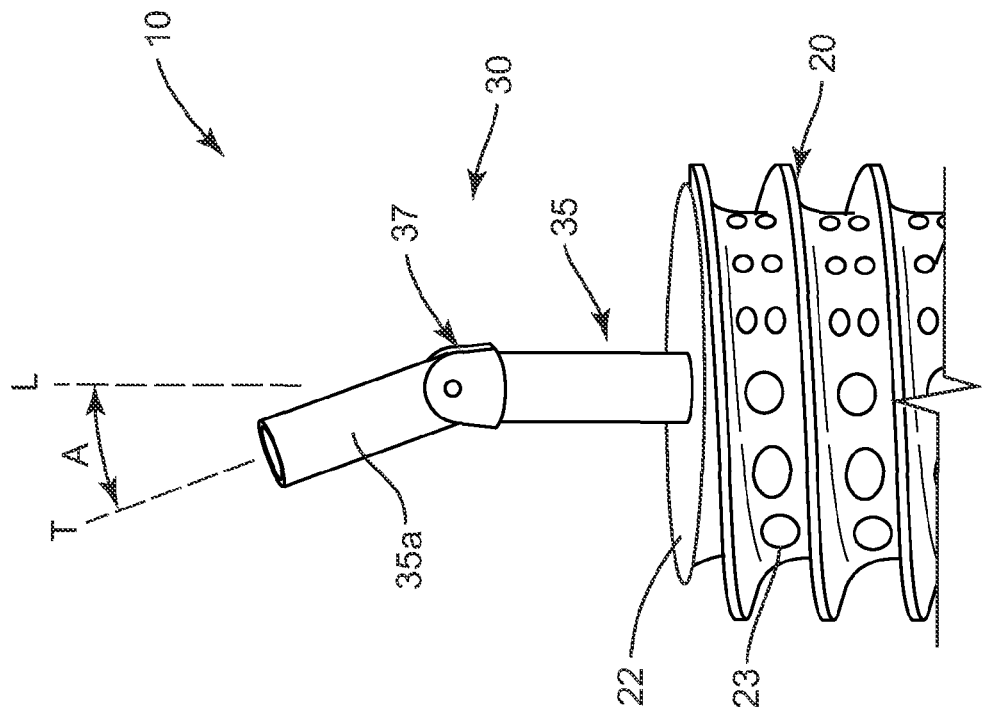
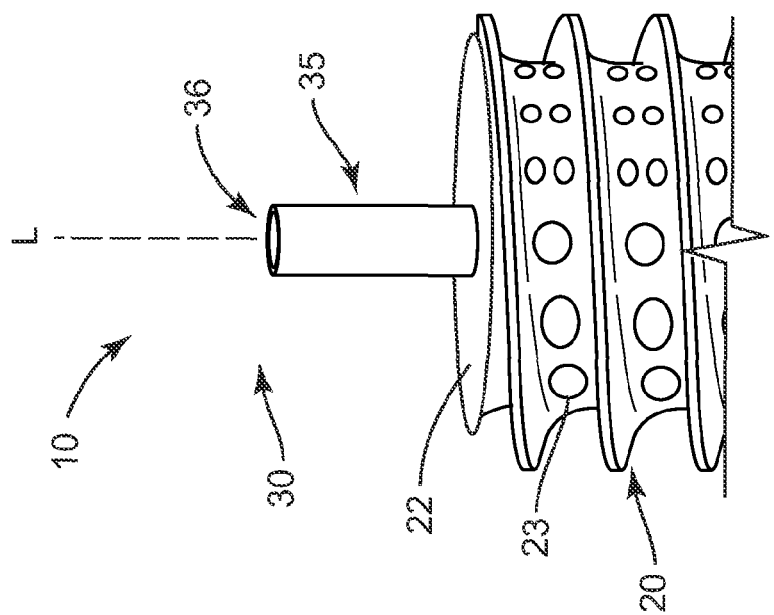
FIG. 4B
FIG. 4A

SACROILIAC TERMINAL ANCHOR DEVICE AND METHOD

BACKGROUND

The present invention relates in general to spinal systems and in particular to a spinal stabilization apparatus and method utilizing sacroiliac constructs. To stabilize a spinal system including a spinal column, the extent of displacement between adjacent vertebrae in the spinal column may be reduced, and/or each pair of adjacent vertebrae may be maintained in a desired spatial relationship. In some cases, rods may be provided that are adapted to extend within the vicinity of the spinal system (including, in some instances, the sacrum and/or adjacent portions of the iliac bones), and connectors may be provided that connect one or more of the rods to one or more of the vertebrae in the spinal system and/or to iliac structures on the pelvis. The rods and connectors may assist in providing immobilization and/or stabilization to the spinal system, and/or may serve as an adjunct to fusion of one or more portions of the spinal system. An example of a system for reducing displacement of a vertebra, in which a rod is employed, is disclosed in U.S. Pat. No. 6,248,107 to Foley et al., the disclosure of which is incorporated by reference.

For spinal stabilization systems that include one or more rods connected to screws or other fasteners attaching the stabilization system to the pelvis, the ability to securely fasten at least a portion of the system to one or more portions of the sacroiliac region may be desired and/or required in order to more prevent the construct from pulling out of or fracturing a pelvic or sacral structure, among other desires and/or requirements. In addition, the ability to utilize bone graft or other bone-growth promotion agents to securely fasten at least a portion of the system to one or more portions of the sacroiliac region may also be desired and/or required. For example, a bone graft "cage" assembly may be ideally suited for anchoring a sacroiliac terminal structure in the bony structures of the ala.

As used herein, it is understood that the term "coronal plane" includes any plane of section in the anatomical position that generally passes vertically through the human body and is generally perpendicular to both the median (or sagittal) plane and the horizontal (or axial or transverse) plane, generally dividing the human body into anterior and posterior sections, and further includes any plane of section in the anatomical position that generally passes vertically through the human body, is generally perpendicular to the horizontal (or axial or transverse) plane, and is generally angularly oriented from the median (or sagittal) plane at an angle of orientation ranging from greater than zero degrees up to and including ninety degrees.

Furthermore, as used herein, it is understood that the term "sagittal plane" includes any plane of section in the anatomical position that generally passes vertically through the human body in the prone position and is generally perpendicular to both the coronal plane and the horizontal (or axial or transverse) plane, generally dividing the human body into left and right sections, and further includes any plane of section in the anatomical position that generally passes vertically through the human body in the prone position, is generally perpendicular to the horizontal (or axial or transverse) plane, and is generally angularly oriented from the coronal plane at an angle of orientation ranging from greater than zero degrees up to and including ninety degrees.

SUMMARY OF THE INVENTION

An apparatus for stabilizing a spinal system is provided that includes a terminal anchor device adapted to be coupled to a bone structure (including, but not limited to the sacrum and ilia). In one embodiment, the terminal anchor apparatus comprises an anchor element adapted to be inserted into a bone structure. The anchor element defines a reservoir adapted to contain a bone-growth promoting material and at least one aperture therein such that the reservoir is in fluid communication with the bone structure. The terminal anchor apparatus also comprises a rod-connecting element extending from a proximal end of the anchor element and adapted to extend outward from the bone structure such that the rod-connecting element is configured for operably engaging at least a portion of a rod when the rod extends within a vicinity of the spinal system and the bone structure.

A method of stabilizing a spinal system is also provided, the method comprising defining a hole in a sacroiliac bone structure and providing a sacroiliac terminal anchor assembly adapted for insertion into the bone structure. As noted herein, the terminal anchor assembly may comprise an anchor element adapted to be inserted into a bone structure, wherein the anchor element defines a reservoir adapted to contain a bone-growth promoting material and at least one aperture therein such that the reservoir is in fluid communication with the bone structure. The anchor assembly also comprises a rod-connecting element extending from a proximal end of the anchor element and adapted to extend outward from the bone structure such that the rod-connecting element is configured for operably engaging at least a portion of a rod when the rod extends within a vicinity of the spinal system and the bone structure. The method further comprises packing the reservoir of the anchor element with the bone-growth promoting material, placing the sacroiliac terminal anchor assembly in the hole defined in the sacroiliac bone, and inserting at least a portion of a rod into a channel defined in the rod-connecting element by moving the rod in a first sagittal plane, such that the rod-connecting element operably engages at least a portion of a rod when the rod extends within a vicinity of the spinal system.

BRIEF DESCRIPTION OF THE DRAWINGS

FIG. 4*a* is a partial perspective view of a terminal anchor apparatus according to one embodiment wherein the rod-connecting element comprises a post.

FIG. 4*b* is a partial perspective view of a terminal anchor apparatus according to one embodiment wherein the rod-connecting element comprises an angulating post.

DETAILED DESCRIPTION

Figure 7:
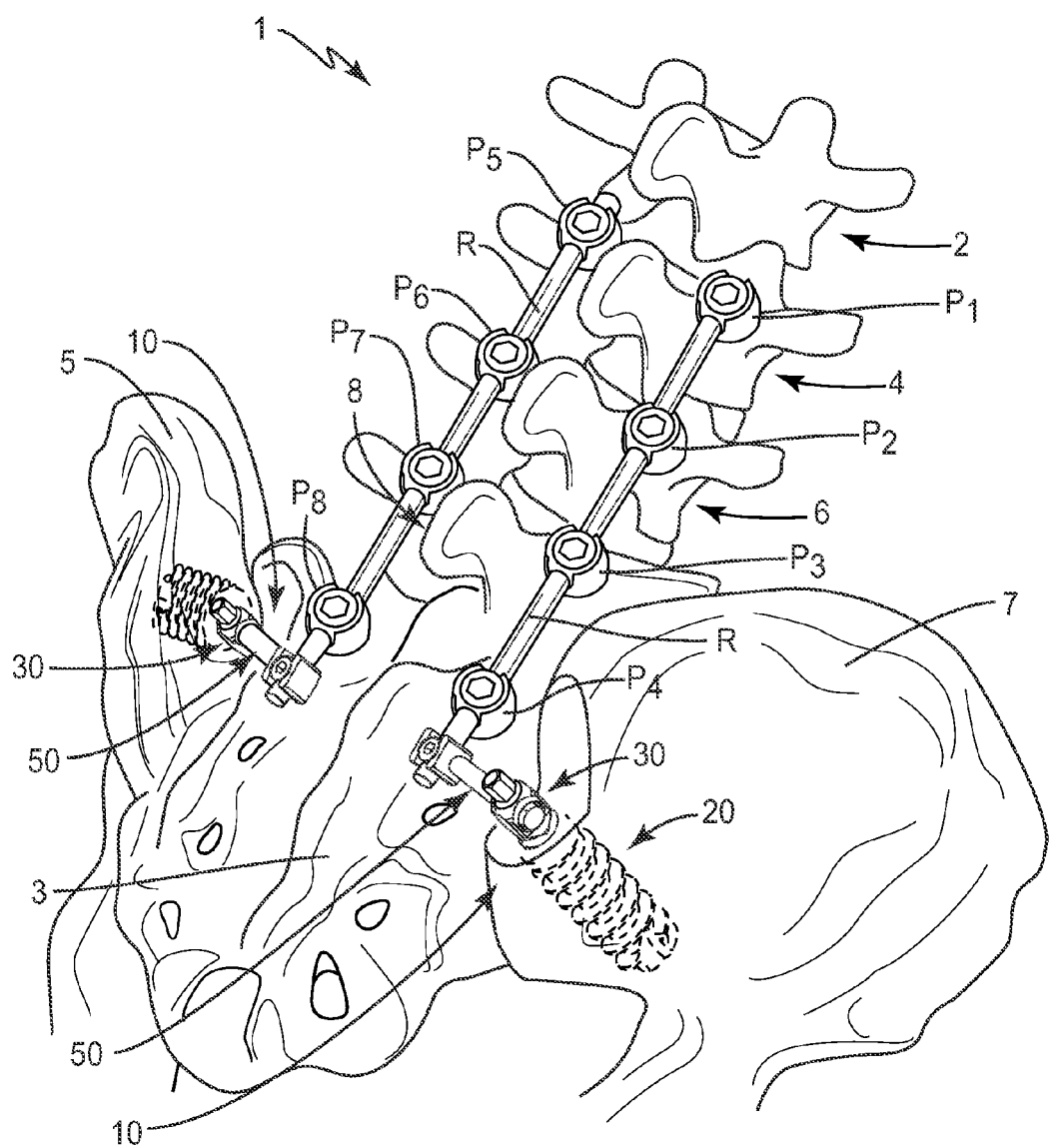
FIG. 7 is a perspective view of an apparatus for stabilizing a spinal system comprising a terminal anchor apparatus according to one embodiment, wherein the terminal anchor apparatus is engaged with a portion of the iliac crest.
Figure 8:
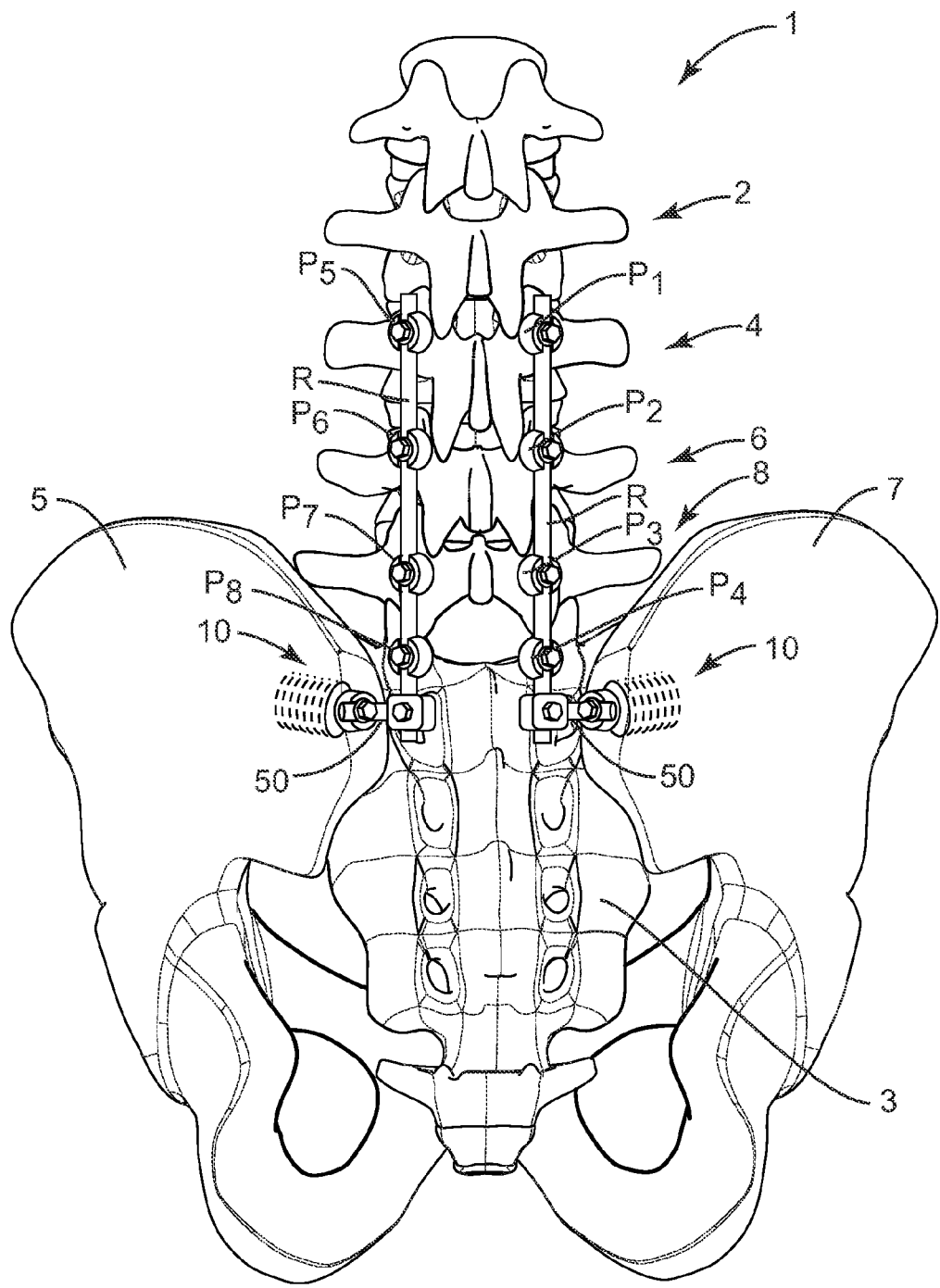
FIG. 8 is a perspective view of an apparatus for stabilizing a spinal system comprising a terminal anchor apparatus according to one embodiment, wherein the terminal anchor apparatus is engaged with a portion of the ilia.

Referring to FIGS. 7 and 8, a spinal system is generally referred to by the reference numeral 1 and includes vertebrae 2, 4, 6, 8, sacrum 3, and ilia 5,7. It is understood that the spinal system 11 includes a human spinal column composed of various types of vertebrae, of which the vertebrae 2, 4, 6 and 8 are a part, and ligaments and/or other natural and/or artificial structures connected to and/or extending between one or more of the vertebrae. Also shown is the sacrum 3, and ilia 5,7 making up the sacroiliac bone structure in the vicinity of the spinal system 1. Rods R extend within the vicinity of the spinal system 1 and the sacroiliac bone structure in a spaced relation. Fasteners, in the form of pedicle screws P1-P8, are threadably engaged with and extend from the pedicles on both sides of vertebrae 2, 4, 6 and 8, respectively. In addition, a fastener, in the form of a terminal anchor apparatus 10 is threadably engaged with and extend from the ilia 5,7 of the sacroiliac bone structures.

As shown generally in FIGS. 7 and 8, pedicle screws P1, P2, P3, P4, P5, P6, P7 and P8 are coupled to the rod R by set screws engaged with saddles, screw "tulips" and/or other connecting elements. Likewise, connector 50 may be engaged with the terminal anchor apparatus 10, and may be coupled to the rod R, thereby connecting the terminal anchor apparatus 10 to the rod R. In some embodiments, the connector 50 is coupled to the rod 18 via a second fastener 52 (which may include, but is not limited to, a set screw as shown generally in FIGS. 6A and 6B). In other embodiments, the terminal anchor apparatus 10 may comprise a rotatable and/or angulating rod-connecting element 30 (see FIGS. 1 and 2, for example) coupled to a proximal end 22 of the anchor element 20. In some such embodiments, the rod-connecting element 30 may be configured for directly receiving the rod R without the need for a separate connector 50.

Figure 1:
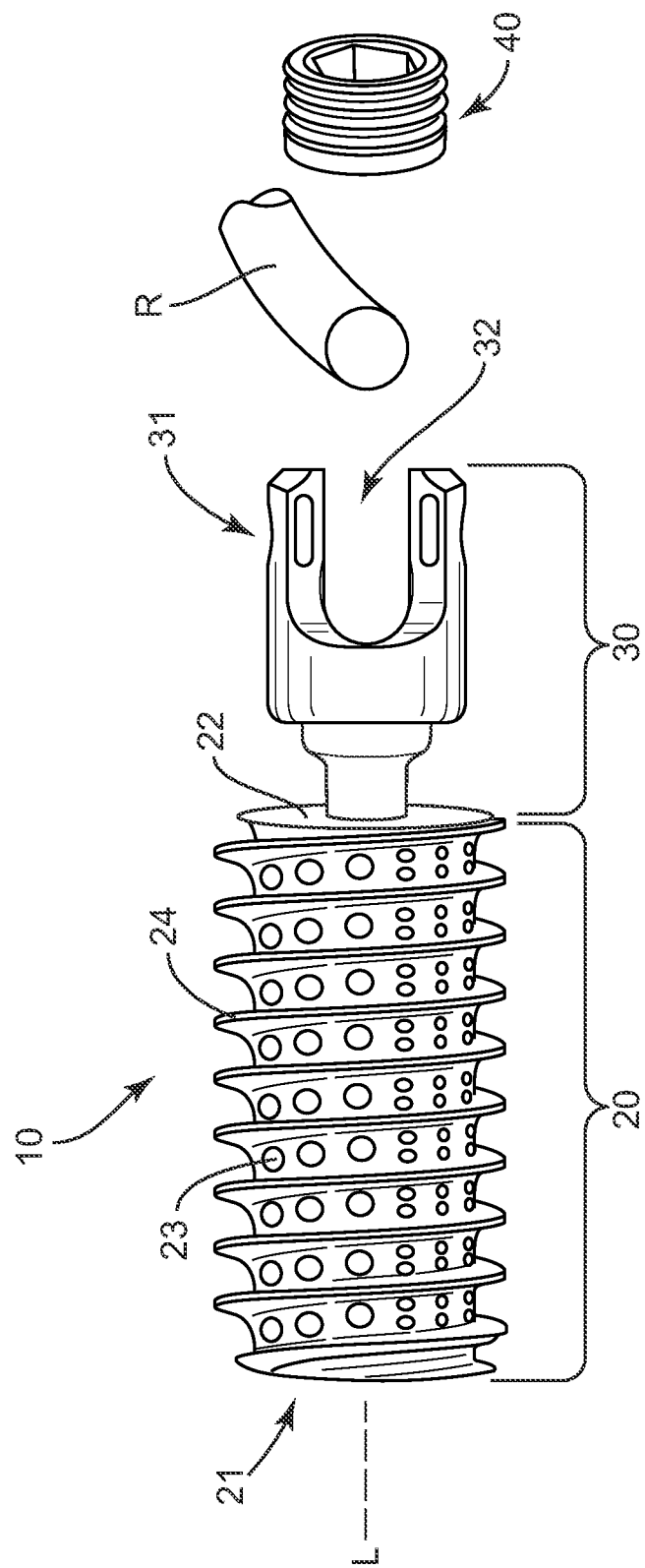
FIG. 1 is a perspective view of a terminal anchor apparatus according to one embodiment.

Referring to FIG. 1, one embodiment of a terminal anchor apparatus 10 is shown for stabilizing a spinal system 1. The terminal anchor apparatus 10 comprises an anchor element 20 adapted to be inserted into a bone structure (such as the ilia 5,7, sacrum 3) as shown generally in FIGS. 7 and 8). In some embodiments, the terminal anchor apparatus 10 may also be implanted into and/or across the sacroiliac (SI) joint. The anchor element 20 has a distal end 21 and a proximal end 22 and extends along a longitudinal axis L. Anchor element 20 is shown herein as generally circular or ovoid in cross-section generally orthogonal to longitudinal axis L. The anchor element 20 may be defined by a first outer diameter wherein, in some embodiment, the first diameter of the anchor element 20, may be greater than a corresponding outer diameter of rod-connecting element 30 described further herein. As shown generally in FIG. 5, the anchor element 20 defines a reservoir 26 adapted to contain a bone-growth promoting material. For example, the anchor element 20 may be formed from the components of an inter-vertebral implant cage defining the reservoir 26 adapted to contain bone-growth promoting material that may include, but is not limited to: allograft, autograft (including native bone and/or bone harvested from the iliac bone structures) xenograft, and/or various types of bone morphogenetic protein (BMP). As shown in FIG. 1, the anchor element 20 defines at least one aperture 23 therein such that the reservoir 26 is in fluid communication with the bone structure via the at least one aperture 23 (thereby allowing the bone-growth promoting material to come into contact with the bone structures of the ilia 5, 7 or sacrum 3 where the terminal anchor apparatus 10 may be implanted by a surgeon). The anchor element 20 may be formed from a variety of inert and/or biocompatible engineering materials including, but not limited to: polymers, polymer blends, metals, alloys and/or combinations thereof.

Figure 2:
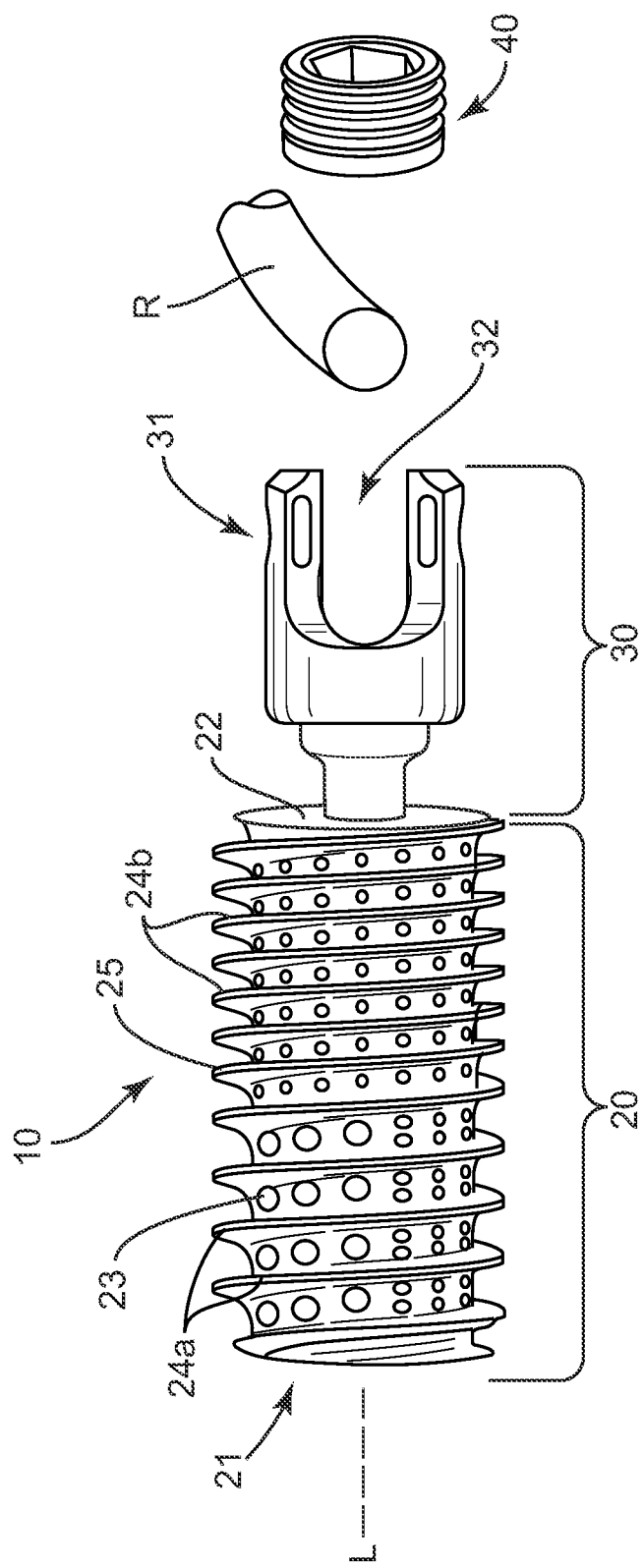
FIG. 2 is a perspective view of a terminal anchor apparatus according to one embodiment wherein the anchor element comprises a dual-thread pattern.
Figure 5:
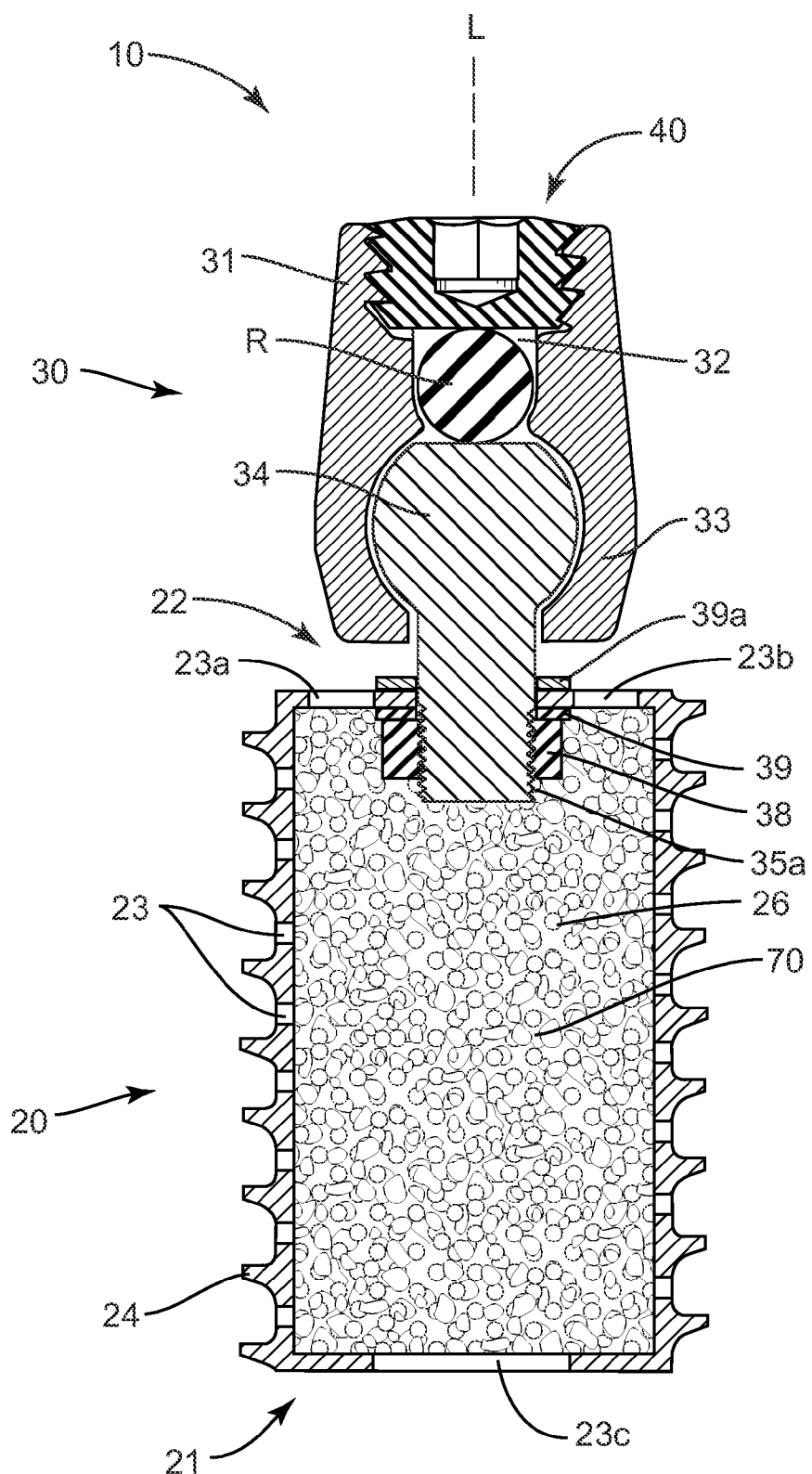
FIG. 5 is a cross-sectional view of a terminal anchor apparatus according to one embodiment.

As shown in FIGS. 1 and 2, the anchor element 20 may define a plurality of apertures 23 having a variety of diameters optimized for the type of bone structure 3, 5, 7 into which the terminal anchor apparatus 10 is placed and/or for the type of bone-growth promoting material placed into the reservoir 26 of the anchor element 20. For example, one aperture 23 diameter and/or configuration may be suitable for fluid communication with cortical bone that may be present on the surface of the bone structure 3, 5, 7 while another aperture 23 diameter and/or configuration may be suitable for fluid communication with trabecular and/or cancellous bone that may be present in the interior of the bone structure 3, 5, 7. As shown generally in FIGS. 1 and 2, the apertures 23 may comprise a series of substantially-round and/or ovoid holes defined in the anchor element 20. The apertures 23 may be defined in a single row and/or multiple rows between adjacent threads 24 of a thread pattern that may be disposed on an outer surface of the anchor element 20. The apertures 23 may also be placed, sized, and/or shaped to suit the type of bone-growth promoting material placed into the reservoir 26. For example, larger apertures 23 may allow for better communication (and more rapid bone growth) between the reservoir 26 and the surrounding bone structure 3, 5, 7. Such larger apertures 23 may also be adequate to contain larger pieces of allograft, autograft and/or other bone components. However, smaller apertures 23 in a denser concentration may preserve fluid communication between the reservoir 26 and the surrounding bone structure 3, 5, 7 while still allowing for the containment of smaller particles of bone-growth promoting material 70 (see FIG. 5, for example). As shown in FIG. 5, the anchor element 20 may define an additional plurality of apertures 23a, 23b, 23c having a variety of diameters in the proximal end 22 and the distal end 21 of the anchor element 20. The apertures 23a, 23b, 23c may be useful in establishing communication between the reservoir 26 and the surrounding bone structure. Furthermore, the various proximal and/or distal apertures 23a, 23b, 23c may also provide openings through which a clinician may pack bone-growth promoting material 70 into the reservoir 26 prior to the implantation of the terminal anchor apparatus 10.

As shown in FIGS. 1 and 2, the anchor element 20 may comprise a thread pattern 24 disposed on an outer surface thereof. The threads 24 may be configured to interact with a tapped hole defined in the bone structure 3, 5, 7 by a surgeon in preparation for the implantation of the terminal anchor apparatus 10. The threads 24 may comprise compressive threads suitable for compressing the bone into which the anchor element 20 may be threaded. Furthermore, it should be understood that the threads 24 may comprise a variety of cross-sectional shapes, pitches, thread densities, and whose design may be optimized for various types of bone applications. For example, in some such embodiments, the thread pattern 24 may comprise a dual-thread arrangement wherein a proximal end of the anchor element 20 has a thread density greater than a distal end of the anchor element 20. This configuration may allow the anchor element 20 to more effectively grip the various types of bone that it may encounter upon implantation into the bone structure 3, 5, 7. For example, the surface bone of the bone structure 3, 5, 7 may comprise comparatively-dense cortical bone that may require a similarly-dense thread pattern to adequately grip and/or compress the bone. Furthermore, interior bone of the bone structure 3, 5, 7 may comprise less-dense trabecular and/or cancellous bone that may require a relatively less-dense thread pattern to grip and/or compress the bone. Therefore, in some such embodiments as shown in FIG. 2, the thread pattern 24 comprises a first thread portion 24a having a first pitch, the first thread portion extending from the distal end 21 of the anchor element 20 to the proximal end 22 of the anchor element 20. The thread portion 20 may also comprise a second thread portion 24b disposed between adjacent threads of the first thread portion 24a and having the first pitch. In order to increase the overall thread density at a proximal portion of the anchor element 20, the second thread portion 24b may extend from an intermediate point 25 disposed between the distal end 21 of the anchor element 20 and the proximal end 22 of the anchor element 20 to the proximal end 22 of the anchor element 20. In such embodiments, the first thread portion 24a results in a distal thread density between the distal end 21 of the anchor element 20 and the intermediate point 25, and the combination of the first thread portion 24a and the second thread portion 24b results in a proximal thread density between the intermediate point 25 and the proximal end 22 of the anchor element 20, wherein the proximal thread density is higher than the distal thread density.

The terminal anchor apparatus 10 also comprises a rod-connecting element 30 extending from the proximal end 22 of the anchor element 20. As shown generally in FIGS. 7 and 8, the rod-connecting element 30 is adapted to extend outward from the bone structure (including but not limited to the ilia 5,7 and/or sacrum 3). The rod-connecting element 30 may comprise a variety of different inert and/or biocompatible materials suitable for connecting to and/or receiving a spinal rod R. For example, the rod-connecting element 30 may incorporate engineering materials including, but not limited to: stainless steel, titanium, cobalt-chrome, polymer and/or combinations thereof. The rod-connecting element 30 has a second outer diameter (extending radially outward from longitudinal axis L) and is configured for operably engaging at least a portion of a rod R when the rod R extends within a vicinity of the spinal system 1 and the bone structure (3, 5 and 7, for example, as shown in FIGS. 7 and 8).

As shown herein (see FIG. 5, for example), the first outer diameter of the anchor element 20 may, in some embodiments, be larger than the second outer diameter of the rod-connecting element 30 such that the anchor element 20 has adequate capacity to contain bone-growth promoting material suitable for initiating bone growth and integration of the anchor device 20 into the bone structure 3, 5, 7 after implantation of the terminal anchor apparatus 10. In this way, the terminal anchor apparatus 10 described herein may be superior to conventional iliac screws for securely anchoring a sacroiliac surgical construct by allowing for the use of bone-growth promoting material 70 within the insertion site of the anchor element 20 of the terminal anchor apparatus 10.

It should be understood that the rod-connecting element 30 may be operably engaged with the anchor element 20 via a number of different techniques. For example, in some embodiments, the at least a portion of the rod-connecting element 30 (such as the post 35) may be integrally formed with the anchor element 20. In other embodiments, such as that shown generally in FIG. 5, the post 35 of the rod-connecting element 30 may be threaded and/or otherwise inserted into a complementary aperture formed in the proximal end 22 of the anchor element. In such embodiments, the post 35 may comprise a plurality of threads 35a suitable for receiving and/or operably engaging a nut 38 that may act to secure the post 35 to the anchor element 20. In some embodiments, a washer 39 may be inserted between the nut 39 and an interior surface of the anchor element 20 in order to more securely fasten the rod-connecting element 30 with the anchor element 20. In some embodiments, the washer 39 may be integrally formed with the post 35 to form a flange that may be attached via adhesive and/or mechanical fasteners to the anchor element 20. In some embodiments, the post 35 may also comprise an upper flange 39a that may cooperate with the nut 38 and washer 39 to grip the proximal end 22 of the anchor element 20 therebetween.

As shown herein (see FIG. 1, for example) the rod-connecting element 30 may comprise a rod-receiver 31 (including but not limited to a "tulip"-style fixed and/or multi-axial pedicle screw head found in the CD Horizon Legacy® or the CD Horizon Solera® lines of spinal instrumentation developed by Medtronic Spinal and Biologics of Memphis, Tenn.). The rod-receiver 31 may define a channel 32 having an open top such that at least a portion of a spinal rod R may be inserted into the channel by moving the rod R in a first sagittal plane when the patient is oriented generally in a prone surgical position to allow surgical access to the spinal system 1. As shown in FIGS. 1 and 2, the terminal anchor apparatus 10 may further comprise a set fastener 40 configured to be operably engaged with the rod-receiver 31 such that the rod R is secured in the channel 32 by the cooperation of the rod-receiver 31 and the set fastener 40.

Figure 3A:
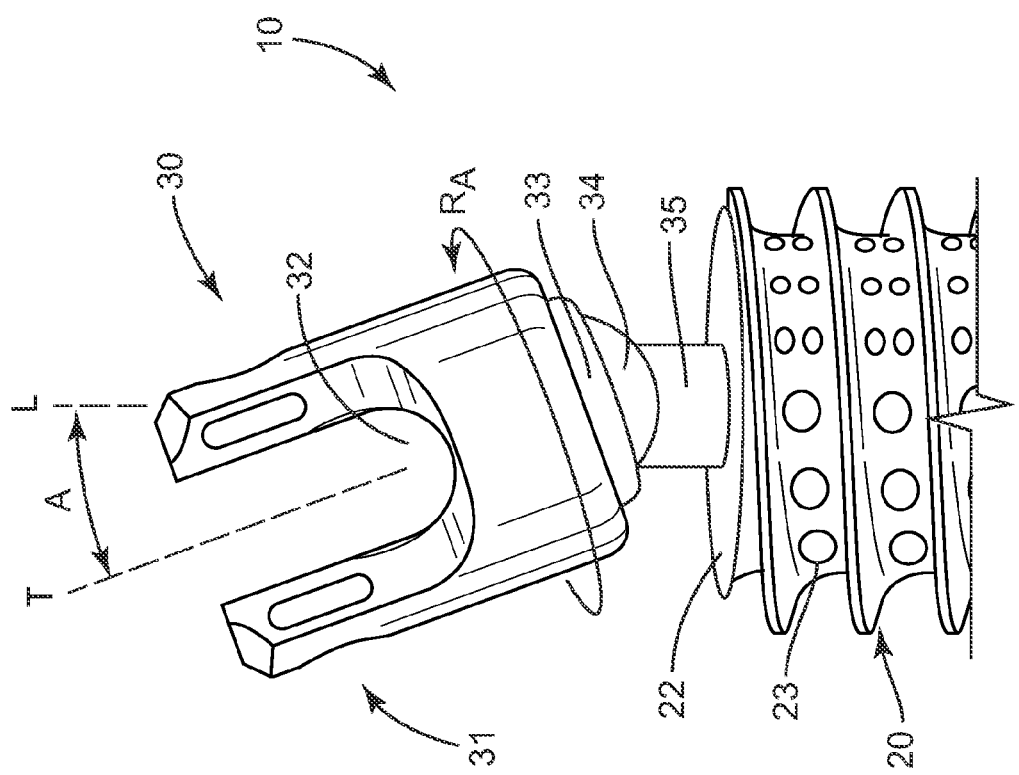
FIG. 3*a* is a partial perspective view of a terminal anchor apparatus according to one embodiment wherein the rod-connecting element comprises a multi-axial head.
Figure 3B:
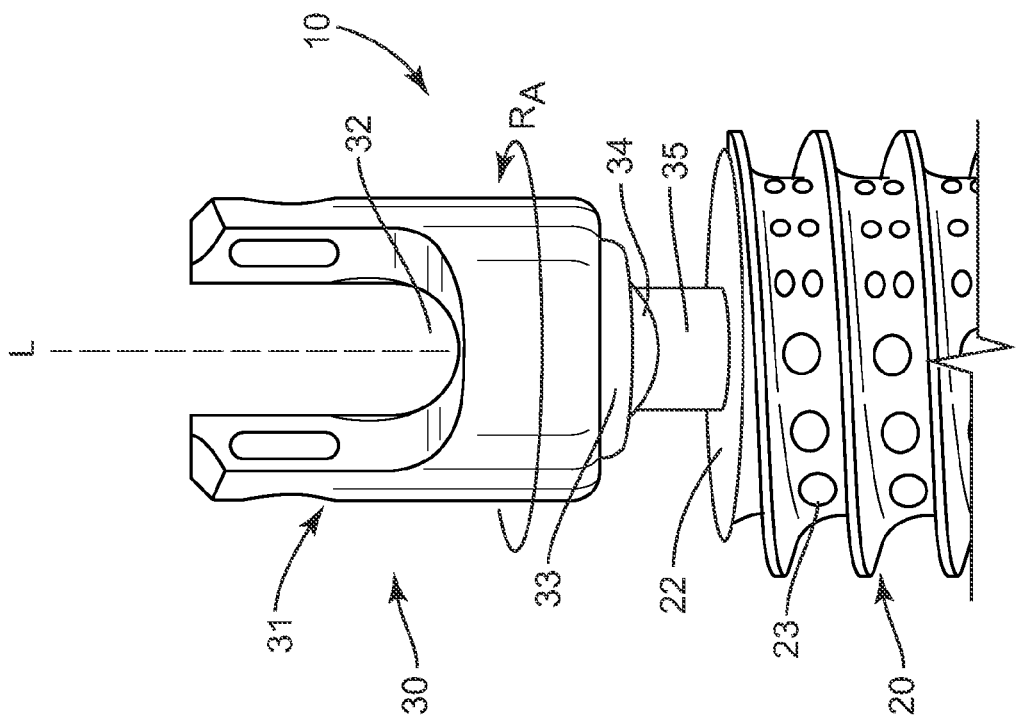
FIG. 3*b* is a partial perspective view of the terminal anchor apparatus shown in FIG. 3*a* wherein the rod-connecting element is shown angulated relative to the anchor element.

As shown in FIG. 3A, the rod receiver 31 may be rotatable 360 degrees in place relative to the anchor element 20 to allow for complete angular adjustability of the rod-connecting element 30 relative to the anchor element 20 (which may be substantially fixed in the bone structure). Such embodiments may allow for rotation (RA) as shown in FIGS. 3A and 3B about the longitudinal axis L of the terminal anchor apparatus 10. While the rotation (RA) is shown as a counterclockwise rotation in FIGS. 3A and 3B, it should be understood that the rod receiver 31 may be rotatable 360 degrees in place in both clockwise and counterclockwise directions in place relative to the anchor element 20 to fully adjust and, in some embodiments, fix the direction of extension of at least a portion of the rod R in a first coronal plane.

In other embodiments, as shown in FIG. 3B, the rod-receiver 31 may be tiltable relative to the longitudinal axis L of the anchor element 20 in order to allow for a wider range of positions to account for differences in morphology of the bone structure 3, 5, 7 and/or to better allow for easier engagement of the rod R between the terminal anchor apparatus 10 and any combination of pedicle screws P1-P8 (see FIG. 7, for example) that may be used to fully instrument a spinal system 1 as part of a surgical procedure. As noted herein, the rod-receiver 31 may comprise a multi-axial screw (MAS) "tulip"-style screw head found in the CD Horizon Legacy® or the CD Horizon Solera® lines of spinal instrumentation developed by Medtronic Spinal and Biologics of Memphis, Tenn. As shown in FIG. 3B, the rod-receiver 31 may thereby be tilted to a tilt axis T that is separated from the longitudinal axis L of the terminal anchor apparatus 10 by angle A.

As shown in FIG. 5, the rotatable and/or tiltable rod-receiver 31 embodiments of the terminal anchor apparatus 10 may comprise a ball 34 engaged with a post 35 extending from the proximal end 22 of the anchor element 20. The ball 34 may be inserted into a collar 33 formed at a distal end of the rod-receiver 31 such that the collar 33 is rotatable and/or tiltable about the ball 34. Furthermore, the rod-receiver 31 selectively fixed at an angle A and at a rotational position RA relative to the ball 34 (and the anchor element 20) by inserting the rod R into the channel 32 and securing the rod in the channel 32 via the engagement of a set screw 40 with a proximal end of the rod-receiver 31. The set screw 40 may therefore be brought to bear against a substantially flat upper surface of the ball 34 (as shown in the exemplary cross-section of FIG. 5) by the set screw 40 in order to fix the rod-receiver 31 at an angle A and at a rotational position RA relative to the ball 34 (and the anchor element 20).

Referring to FIG. 4A, in some embodiments, the terminal anchor apparatus 10 may comprise a rod-connecting element 30 embodied as a post 35 adapted to operably engage a connector device (not shown) for operably engaging at least a portion of the rod R. For example, the post 35 may serve as an attachment point for a variety of angulating and/or fixed connector devices including, but not limited to the TSRH-3D® small, medium and large connectors and TSRH-3D® 90-degree offset connectors developed by Medtronic Spinal and Biologics of Memphis, Tenn. In such embodiments, the post 35 may comprise a drive aperture 36 (including, not limited to: a female Torx® interface, a female hex drive interface) that may allow a surgeon to drive the terminal anchor apparatus 10 into a hole defined in the bone structure 3, 5, 7 by rotating the post 35 and the anchor element 20.

In other embodiments, as shown in FIG. 4B, the terminal anchor apparatus 10 may also comprise a post 35 that is pivotable or tiltable relative to the longitudinal axis L of the anchor element 20. For example, such embodiments may comprise a post 35 having a pivot 37 attached to a proximal end thereof, and a pivotable post element 35a operably engaged with the pivot 37 such that the pivotable post element 35a may be pivotable relative to the longitudinal axis L of the anchor element. Such pivotable embodiments may be compatible with a variety of components and instruments available from the TSRH-3D® PLUS MPA™ multi-planar screw system developed by Medtronic Spinal and Biologics of Memphis, Tenn.

Figure 6A:
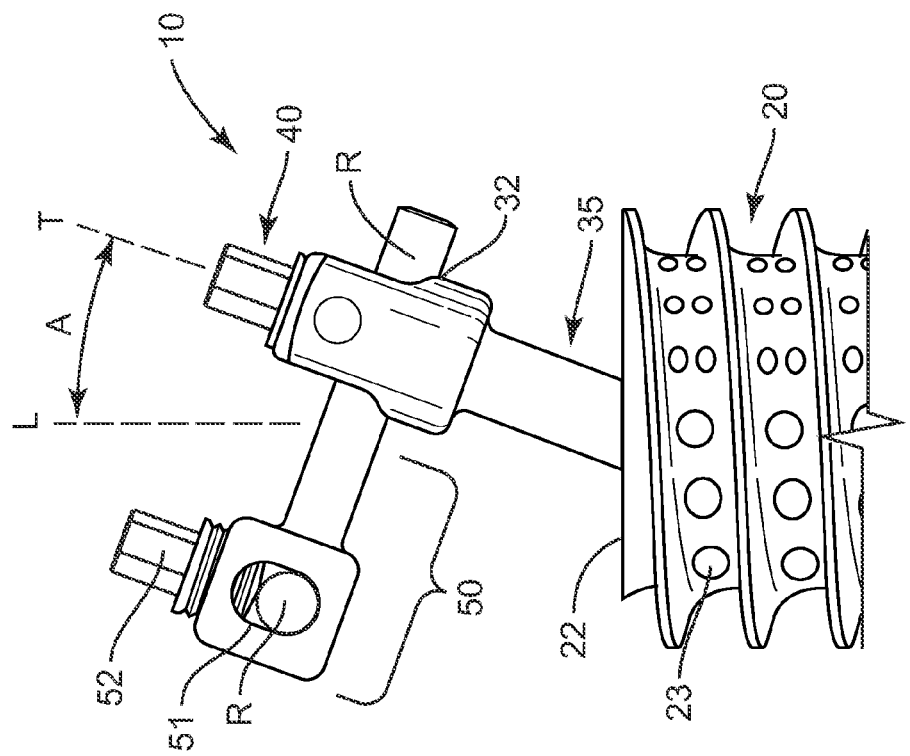
FIG. 6*a* is a partial perspective view of a terminal anchor apparatus according to one embodiment wherein the rod-connecting element comprises a post defining a lateral channel for receiving a connector element.
Figure 6B:
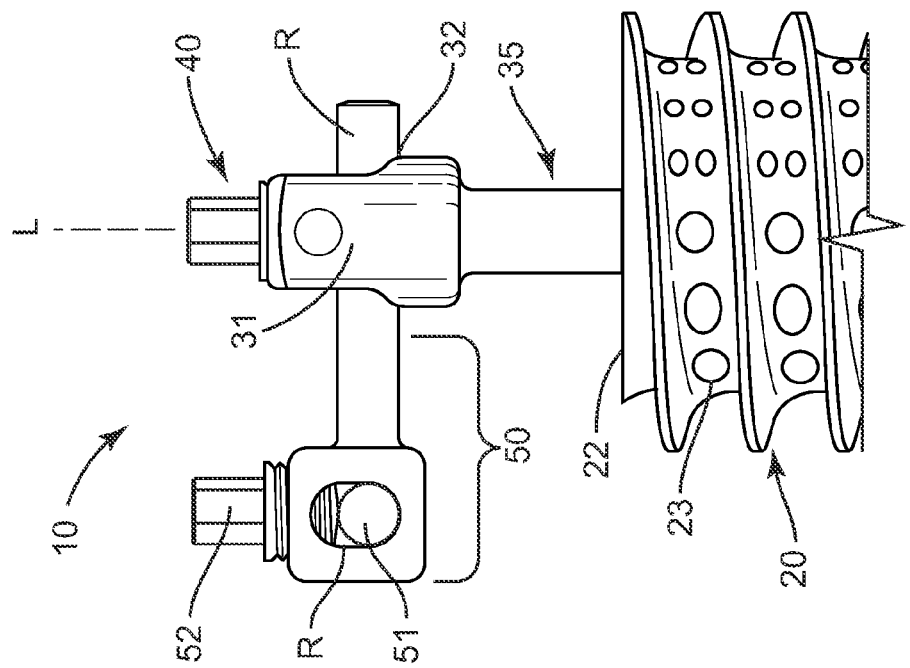
FIG. 6*b* is a partial perspective view of a terminal anchor apparatus according to one embodiment wherein the rod-connecting element comprises a fixed-angle post defining a lateral channel for receiving a connector element.

Referring now to FIGS. 6A and 6B, the terminal anchor apparatus may, in some embodiments also comprise a rod-connecting element 30 (such as the post 35) defining an aperture 32 extending therethrough. For example, the post 35 may comprise a rod-receiver 31 wherein the rod-receiver 31 has a closed top defining the aperture 32. A set screw 40 may be engaged with a threaded aperture defined in a top portion of the rod-receiver 31 in order to secure a rod-portion of a connector element 50 therein. The connector element 50 may therefore allow for lateral positioning of a spinal rod R (see FIGS. 7 and 8, for example) relative to the terminal anchor element 10. The connector element 50 may comprise a variety of lateral ilio-sacral connector elements having rod portions that are compatible with the rod-connecting element 30 of the terminal anchor element 10. As shown in FIG. 6A, the connector element 50 may define a rod-receiver aperture 51 sized to receive the spinal rod R. The connector element 50 may also comprise a set screw 52 configured to secure the spinal rod R in the rod-receiver aperture 51 in order to complete an ilio-sacral terminal construct such as that shown generally in FIG. 7 and/or FIG. 8. As shown in FIG. 6B, in some such embodiments, the rod-connecting element 30 may comprise a post 35 and rod-receiver 31 that are tilted at an angle A relative to the longitudinal axis L of the terminal anchor element 10. Such embodiments may be useful in some surgical constructs wherein the terminal anchor element 10 is inserted into a bony structure 3, 5, 7 that is displaced at an angle relative to an axis defined by the spinal system 1.

Various methods for stabilizing a spinal system 1 are also provided herein, wherein the method first comprises defining a hole in a sacroiliac bone structure (including, but not limited to the ilia 5, 7, sacrum 3, and/or the sacroiliac (SI) joint). The hole may be defined by a surgeon using a variety of techniques and instruments, including but not limited to surgical taps, reamers, drills, bits, and/or other devices. In some embodiments, the method may comprise defining the hole in the sacroiliac bone structure 3, 5, 7 using a tap having threads matching a thread pattern 24 defined on an outer surface of a terminal anchor element 10 such as that shown generally in FIG. 2. For example, the defining step may comprise defining a female thread pattern in the hole in the sacroiliac bone structure 3, 5, 7, and the providing step described further herein, may further comprise providing a male thread pattern 24 disposed on an outer surface of the anchor element 20 wherein the male thread pattern 24 is configured for engaging the female thread pattern to secure the anchor element 20 in the hole. As described herein, the threads 24 may be formed to compress bone material so as to more securely fasten the anchor element 20 within the bone structure 3, 5, 7.

In method embodiments, wherein the anchor element 20 is provided with a male thread pattern, the pattern may comprise (see FIG. 2) a first thread portion 24a having a first pitch, the first thread portion 24a extending from the distal end 21 of the anchor element 20 to the proximal end 22 of the anchor element 20. The pattern may further comprise a second thread portion 24b disposed between adjacent threads of the first thread portion 24a and also having the first pitch. The second thread portion 24b extends from an intermediate point 25 disposed between the distal end 22 of the anchor element 20 and the proximal end 21 of the anchor element 20 to the proximal end 22 of the anchor element 20. In such embodiments, the first thread portion 24a results in a distal thread density between the distal end 21 of the anchor element 20 and the intermediate point 20. Furthermore, the combination of the first thread portion 24a and the second thread portion 24b results in a proximal thread density between the intermediate point 25 and the proximal end 22 of the anchor element 20, wherein the proximal thread density is higher than the distal thread density.

Various method embodiments comprise providing a sacroiliac terminal anchor assembly (such as the various embodiments of the terminal anchor element 10, described herein). As noted herein with respect to FIGS. 1-8, the sacroiliac terminal anchor assembly may comprise an anchor element 20 having a distal end 21, a proximal end 22 and a longitudinal axis L. Furthermore, the anchor element 20 may define a reservoir 26 therein (see FIG. 5) adapted to contain a bone-growth promoting material 70. The anchor element 20 also defines at least one aperture 23 (see also apertures 23a, 23b, 23c shown in FIG. 5) therein such that the reservoir 26 is in fluid communication with an exterior of the anchor element 20. The sacroiliac terminal anchor assembly may further comprise a variety of different rod-connecting elements 30 as described in detail herein. The rod-connecting element 30 extends from the proximal end 22 of the anchor element 20 and may be adapted to extend outward from the bone structure 3, 5, 7 when the anchor element 20 is inserted into the hole defined in the bone structure 3, 5, 7. Furthermore, the rod-connecting element 30 comprises at least one type of rod-receiver 31 (including, but not limited to a post 35 as shown in FIG. 4A suitable for interface with a connector that may, in turn, be configured for receiving a spinal rod R). In other embodiments, as shown in FIGS. 1-2, 3A and 3B, the rod-receiver 31 may define a channel 32 having an open top configured for receiving the rod R therein (see FIG. 1, for example).

The method embodiments further comprise packing the reservoir 26 of the anchor element 20 with the bone-growth promoting material 70 (see FIG. 5, for example). The packing step may comprise packing bone-growth promoting material 70 through apertures 23a, 23b located on a proximal end 22 of the anchor element 20 and/or packing bone-growth material 70 through aperture 23c located on a distal end 21 of the anchor element. As described herein, the bone-growth promoting material 70 may include, but is not limited to: allograft, autograft, xenograft, and/or bone morphogenetic protein (BMP).

The method embodiments further comprise placing the sacroiliac terminal anchor assembly 10 in the hole defined in the sacroiliac bone structure 3, 5 and/or 7 (see FIGS. 7 and 8, for example) such that the anchor element 20 is disposed substantially within the hole. Thus, the bone-growth promoting material 70 may be in fluid communication with the sacroiliac bone structure 3, 5, 7 via the at least one aperture 23 defined in the anchor element 20. Furthermore, as shown generally in FIGS. 7 and 8, the rod-connecting element 30 extends substantially out of the hole such that the method may further comprise inserting at least a portion of a rod R into the channel 32 defined in the rod-connecting element 30 by moving the rod R in a first sagittal plane, such that the rod-connecting element 30 operably engages at least a portion of the rod R when the rod R extends within a vicinity of the spinal system 1.

As shown in FIGS. 3A and 3B, the rod connecting element 30 (and/or a rod-receiver 31 thereof) may be rotatable (see rotational movement denoted by RA) about the longitudinal axis L of the anchor element 20. In such embodiments, the method may further comprise selectively adjusting the direction of extension of at least a portion of the rod R in a first coronal plane by rotating the rod-connecting element 30 relative to the anchor element 20. Such method embodiments may further comprise locking the direction of extension of the at least a portion of the rod R. For example, the locking step may be accomplished in some embodiments by engaging a set fastener 40 (see FIG. 5) with the rod-receiver 31 in order to "lock down" the rod R against a flat top portion of the ball 34 engaged with a proximal end of the post 35.

It is understood that any foregoing spatial references, such as "top," "bottom." "upper," "lower," "above," "below," "between," "vertical," "angular," "up," "down," "right," "left," etc., are for the purpose of illustration only and do not limit the specific orientation or location of the structure described above.

Moreover, it is understood that any of the terminal anchor apparatus 10 embodiments described herein may be used in the iliac bones 5, 7, the sacrum 3, the sacroiliac (SI) joint, in any iliac bone structure and/or in any location, and with any type of vertebra and/or any natural and/or artificial structure extending to or from the vertebra, within the spinal system 1. It is further understood that the cross-sections of the rods R extending within the vicinity of the spinal system 1 may be varied, and that the corresponding cross-sections of the channels 32 of the rod-connecting element 30 into which the rods R may be placed may also be correspondingly varied.

Also, it is understood that each of the above-described embodiments may be combined in whole or in part with one or more of the other above-described embodiments. It is further understood that each of the above-described embodiments may be combined in whole or in part with other components, devices, systems, methods and/or surgical techniques known to those skilled in the art to provide spinal stabilization.

Although exemplary embodiments of this invention have been described in detail above, those skilled in the art will readily appreciate that many other modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A terminal anchor apparatus for stabilizing a spinal system, the apparatus comprising:
   an anchor element adapted to be inserted into a bone structure, the anchor element having a distal end and a proximal end, the anchor element defining a reservoir adapted to contain a bone-growth promoting material, the anchor element defining at least one aperture therein such that the reservoir is in fluid communication with the bone structure via the at least one aperture, the anchor element having a longitudinal axis and a first outer diameter extending radially outward from the longitudinal axis;
   a post element extending from the proximal end of the anchor element, the post element including a ball at a proximal end thereof, wherein the post element is tiltable relative to the longitudinal axis of the anchor element; and
   a rod-connecting element operably engaged with the post element and having an inner surface defining a cavity configured for movable disposal of the ball such that the rod-connecting element is rotatable and tiltable about the ball, the rod-connecting element comprising a rod receiver positioned proximal of a proximal face of the anchor element, the rod-connecting element being adapted to extend outward from the bone structure, the rod-connecting element having a second outer diameter, the rod-connecting element configured for operably engaging at least a portion of a rod when the rod extends within a vicinity of the spinal system and the bone structure;
   wherein the first outer diameter of the anchor element is larger than the second outer diameter of the rod-connecting element.

2. The apparatus of claim 1, wherein the rod receiver defines a channel having an open top such that at least a portion of the rod may be inserted into the channel by moving the rod in a first sagittal plane.

3. The apparatus of claim 2, wherein the rod-receiver is rotatable 360 degrees in place relative to the anchor element to adjust and fix the direction of extension of the at least a portion of the rod in the first coronal plane.

4. The apparatus of claim 2, wherein the rod-receiver is tiltable relative to the longitudinal axis of the anchor element.

5. The apparatus of claim 1, wherein the rod-connecting element defines an aperture extending therethrough.

6. The apparatus of claim 1, wherein the anchor element comprises a thread pattern disposed on an outer surface thereof.

7. The apparatus of claim 6, wherein the thread pattern comprises:
   a first thread portion having a first pitch, the first thread portion extending from the distal end of the anchor element to the proximal end of the anchor element; and a second thread portion disposed between adjacent threads of the first thread portion and having the first pitch, the second thread portion extending from an intermediate point disposed between the distal end of the anchor element and the proximal end of the anchor element to the proximal end of the anchor element;

wherein the first thread portion results in a distal thread density between the distal end of the anchor element and the intermediate point, and wherein the combination of the first thread portion and the second thread portion results in a proximal thread density between the intermediate point and the proximal end of the anchor element, the proximal thread density being higher than the distal thread density.

8. A terminal anchor apparatus for stabilizing a spinal system, the apparatus comprising:

an anchor element adapted to be inserted into a bone structure, the anchor element having a distal end and a proximal end, the anchor element defining a reservoir adapted to contain a bone-growth promoting material, the anchor element defining at least one aperture therein such that the reservoir is in fluid communication with the bone structure via the at least one aperture, the anchor element having a longitudinal axis;

a post element extending from the proximal end of the anchor element, the post element including a ball at a proximal end thereof;

a rod-connecting element having an inner surface defining a cavity configured for movable disposal of the ball such that the rod-connecting element is rotatable and tiltable about the ball, the rod-connecting element being adapted to extend outward from the bone structure, the rod-connecting element comprising a rod-receiver positioned proximal of a proximal face of the anchor element, a distal face of the rod-receiver being spaced apart from a proximal face of the anchor element, the rod receiver defining a channel having an open top such that at least a portion of the rod may be inserted into the channel by moving the rod in a first sagittal plane such that the rod-connecting element operably engages at least a portion of a rod when the rod extends within a vicinity of the spinal system and the bone structure; and a set fastener configured to be operably engaged with the rod-receiver such that the rod is secured in the channel by the cooperation of the rod-receiver and the set fastener, and the anchor element having a first outer diameter and the rod-connecting element having a second outer diameter, wherein the first outer diameter of the anchor element is larger than the second outer diameter of the rod-connecting element.

9. The apparatus of claim 8, wherein the rod-receiver is rotatable 360 degrees in place relative to the anchor element to adjust and fix the direction of extension of the at least a portion of the rod in the first coronal plane.

10. The apparatus of claim 8, wherein the rod-receiver is tiltable relative to the longitudinal axis of the anchor element.

11. The apparatus of claim 8, wherein the anchor element comprises a thread pattern disposed on an outer surface thereof.

12. The apparatus of claim 11, wherein the thread pattern comprises:

a first thread portion having a first pitch, the first thread portion extending from the distal end of the anchor element to the proximal end of the anchor element; and a second thread portion disposed between adjacent threads of the first thread portion and having the first pitch, the second thread portion extending from an intermediate point disposed between the distal end of the anchor element and the proximal end of the anchor element to the proximal end of the anchor element;

wherein the first thread portion results in a distal thread density between the distal end of the anchor element and the intermediate point, and wherein the combination of the first thread portion and the second thread portion results in a proximal thread density between the intermediate point and the proximal end of the anchor element, the proximal thread density being higher than the distal thread density.

* * * * *